(12) United States Patent
Li (10) Patent No.: US 7,658,750 B2
(45) Date of Patent: Feb. 9, 2010

(54) SUTURE ANCHORING SYSTEM AND METHOD

(75) Inventor: Lehmann K. Li, Milford, CT (US)

(73) Assignee: Warsaw Orthopedic, Inc.

( * ) Notice: Subject to any disclaimer, the term of this patent is extended or adjusted under 35 U.S.C. 154(b) by 1052 days.

(21) Appl. No.: 10/803,440

(22) Filed: Mar. 18, 2004

(65) Prior Publication Data

US 2005/0228448 A1 Oct. 13, 2005

(51) Int. Cl.
*A61B 17/04* (2006.01)
(52) U.S. Cl. .................................................. 606/232
(58) Field of Classification Search ................. 606/232
See application file for complete search history.

(56) References Cited

U.S. PATENT DOCUMENTS

| | | | |
|---|---|---|---|
| 4,741,330 A | 5/1988 | Hayhurst | |
| 4,968,315 A | 11/1990 | Gattuma | |
| 5,041,129 A | 8/1991 | Hayhurst et al. | |
| 5,176,682 A | 1/1993 | Chow | |
| 5,203,787 A | 4/1993 | Noblitt et al. | |
| 5,324,308 A | 6/1994 | Pierce | |
| 5,403,348 A | 4/1995 | Bonutti | |
| 5,405,359 A | 4/1995 | Pierce | |
| 5,464,426 A * | 11/1995 | Bonutti | ...................... 606/232 |
| 5,464,427 A | 11/1995 | Curtis et al. | |
| 5,486,197 A | 1/1996 | Le et al. | |
| 5,522,846 A | 6/1996 | Bonutti | |
| 5,549,630 A | 8/1996 | Bonutti | |
| 5,584,862 A | 12/1996 | Bonutti | |
| 5,733,306 A | 3/1998 | Bonutti | |
| 5,810,848 A * | 9/1998 | Hayhurst | .................... 606/144 |
| 5,941,900 A | 8/1999 | Bonutti | |
| 6,056,773 A | 5/2000 | Bonutti | |
| 6,077,292 A | 6/2000 | Bonutti | |
| 6,149,669 A | 11/2000 | Li | |
| 6,152,949 A | 11/2000 | Bonutti | |
| 6,206,886 B1 | 3/2001 | Bennett | |
| 6,287,325 B1 | 9/2001 | Bonutti | |
| 6,309,405 B1 | 10/2001 | Bonutti | |
| 6,312,448 B1 | 11/2001 | Bonutti | |
| 6,364,897 B1 | 4/2002 | Bonutti | |
| 6,428,562 B2 | 8/2002 | Bonutti | |
| 6,656,183 B2 * | 12/2003 | Colleran et al. | ................ 606/72 |

FOREIGN PATENT DOCUMENTS

| | | |
|---|---|---|
| EP | 0 464 480 A1 | 1/1992 |
| EP | 0 236 427 B1 | 8/1993 |
| EP | 0 699 416 A2 | 3/1996 |
| WO | WO 98/07374 | 2/1998 |
| WO | WO 03/096910 A1 | 11/2003 |

\* cited by examiner

*Primary Examiner*—Todd E Manahan
*Assistant Examiner*—Michael G Mendoza (57) ABSTRACT

A suture anchoring system and method includes a plurality of anchor members interconnected to form an anchor assembly with a suture extending therefrom. The anchor assembly has an insertion configuration wherein the anchor members are aligned in a substantially linear arrangement for delivery through an aperture in bodily tissue and an expanded configuration wherein the anchor members are transitioned to a non-linear arrangement to prevent passage of the anchor assembly back through the aperture.

17 Claims, 4 Drawing Sheets

SUTURE ANCHORING SYSTEM AND METHOD

BACKGROUND

The complete or partial detachment of ligaments, tendons or other soft tissues from their associated bones within the body is a relatively common place injury, particularly among athletes and physically active individuals. These types of injuries generally result from excessive stresses being applied to the soft tissues. For example, a tissue detaching injury may occur as the result of a fall, overexertion during a work-related activity, during the course of an athletic event, and/or in association with other situations or physical activities.

In the case of a partial detachment injury, which is commonly referred to under the general term "sprain", the injury will frequently heal itself if given sufficient time and if care is taken not to expose the injury to any undue or extraordinary stress during the healing process. If, however, the ligament or tendon is completely detached from its associated bone or bones, or if it is severed as a result of a traumatic injury, partial or permanent disability may result. Fortunately, a number of surgical techniques exist for reattaching detached tissues and/or completely replacing severely damaged tissues. One such technique involves reattachment of detached tissue using traditional attachment devices such as metal staples, sutures over buttons and/or cancellous bone screws. These types of traditional attachment techniques and devices may also be used to attach tendon or ligament substitutes (sometimes formed of autogenous tissue harvested from other locations in the body) to the desired bone or bones.

Although attempts have been made to provide techniques and devices for forming an attachment to bone or other tissue, there is a general need in the industry to provide an improved suture anchoring system and method. The present invention satisfies this need and provides other benefits and advantages in a novel and unobvious manner.

SUMMARY

The present invention relates generally to an improved suture anchoring system and method. While the actual nature of the invention covered herein can only be determined with reference to the claims appended hereto, certain forms of the invention that are characteristic of the preferred embodiments disclosed herein are described briefly as follows.

In one form of the present invention, a suture anchoring system is provided including at least three anchor members interconnected to form an anchor assembly with a suture extending therefrom. The anchor assembly has an insertion configuration sized for delivery through an aperture in bodily tissue and is transitionable to an expanded configuration sized to prevent passage of the anchor assembly back through the aperture.

In another form of the present invention, a suture anchoring system is provided including at least three anchor members interconnected to form an anchor assembly with a suture extending therefrom. The anchor assembly has an insertion configuration wherein the anchor members are aligned in a substantially linear arrangement for delivery through an aperture in bodily tissue and an expanded configuration wherein the anchor members are transitioned to a non-linear arrangement to prevent passage of the anchor assembly back through the aperture.

In another form of the present invention, a suture anchoring system is provided including at least three anchor members interconnected to form an anchor assembly with a suture extending therefrom. The anchor assembly includes first and second outer anchor members and at least one intermediate anchor member, and has an insertion configuration wherein the anchor members are aligned in a substantially linear arrangement for delivery through an aperture in bodily tissue and an expanded configuration wherein the outer anchor members are drawn toward one another to define a non-linear arrangement to prevent passage of the anchor assembly back through the aperture.

In another form of the present invention, a suture anchoring system is provided including at least three anchor members, means for interconnecting the anchor members to form an anchor assembly with a suture extending therefrom and having an insertion configuration wherein the anchor members are aligned in a substantially linear arrangement for delivery through an aperture in bodily tissue, and means for transitioning the anchor assembly from the insertion configuration to an expanded configuration wherein the anchor members are transitioned to a non-linear arrangement to prevent passage of the anchor assembly back through the aperture.

In another form of the present invention, a suture anchoring system is provided including a plurality of anchor members interconnected to form an anchor assembly with a suture extending therefrom. The anchor assembly has an insertion configuration wherein the anchor members are aligned in a substantially linear arrangement for delivery through an aperture in bodily tissue and an expanded configuration wherein first and second ones of the anchor members are drawn toward one another to define a non-linear arrangement to prevent passage of the anchor assembly back through the aperture. The system further includes an actuating element extending through a first loop structure associated with the first anchor member and through a second loop structure associated with the second anchor member, and wherein the first and second anchor members are drawn toward one another by pulling the actuating element in a direction away from the anchor assembly to at least partially transition the anchor assembly toward the expanded configuration.

In another form of the present invention, a method for anchoring a suture to bodily tissue is provided including providing at least three anchor members interconnected to form an anchor assembly with a suture extending from the anchor assembly, aligning the anchor members in a substantially linear configuration, inserting the anchor members through an aperture in the bodily tissue while in the linear configuration, and transitioning the anchor members from the linear configuration to a non-linear configuration to prevent passage of the anchor assembly back through the aperture.

It is one object of the present invention to provide an improved suture anchoring system and method. Further objects, features, advantages, benefits, and aspects of the present invention will become apparent from the drawings and description contained herein.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended, and that alterations and further modifications to the illustrated devices and/or further applications of the principles of the invention as illustrated herein are contemplated as would normally occur to one skilled in the art to which the invention relates.

Figure 1:
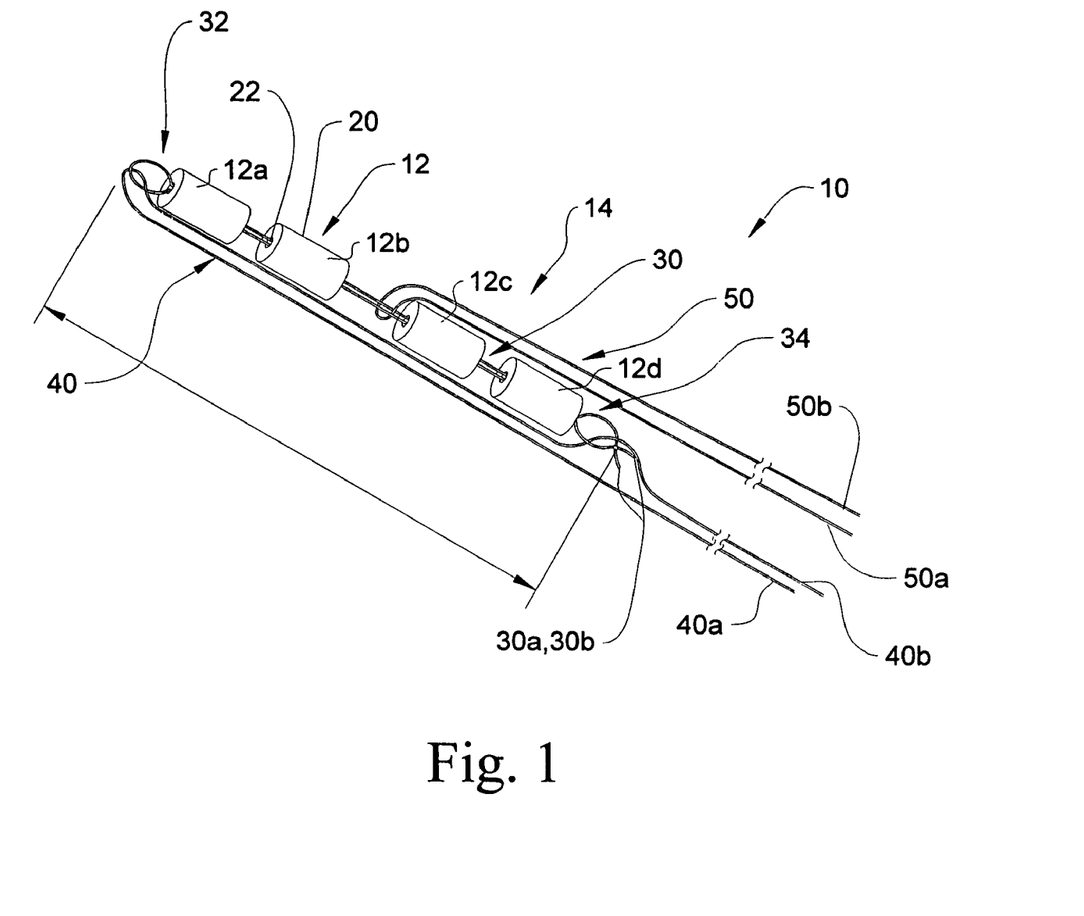
FIG. 1 is a perspective view of a suture anchoring system according to one form of the present invention.

Referring to FIG. 1, shown therein is a suture anchoring system 10 according to one form of the present invention. The anchoring system 10 is generally comprised of a plurality of anchor members 12 and a number of suture elements 14. As will be discussed in greater detail below, in one embodiment of the invention, the anchoring system 10 is configured for anchoring to either hard or soft biological tissue, with the suture elements 14 serving to attach another element or structure (either biological or non-biological) to the biological tissue. As used herein, the term "suture" is broadly defined to include any type of longitudinal element suitable for attachment to biological tissue including, for example, thread, wire, gut or any other type of suture material known to those of skill in the art.

In the illustrated embodiment of the invention, the anchor members 12 each have a generally tubular configuration including a cylindrical wall 20 and defining an axial passage or channel 22 extending therethrough. However, it should be understood that other shapes and configurations of the anchor members 12 are also contemplated as falling within the scope of the present invention including, for example, a rectangular, triangular, polygonal or spherical configuration, or any other suitable shape or configuration. The anchor members 12 are preferably formed of a bio-compatible material. In one embodiment, the anchor members 12 are formed of metallic material such as stainless steel or a stainless steel alloy, titanium or a titanium alloy, a shape-memory alloy, or any other suitable metallic material. However, the use of other materials is also contemplated, including polymeric or ceramic materials, resorbable materials, bioabsorbable materials, or bone or bone substitute materials.

In the illustrated embodiment of the invention, the suture anchoring system 10 includes four anchor members 12a, 12b, 12c and 12d that are coupled together or interconnected to form an anchor assembly. However, it should be understood that the anchoring system 10 may include any number of anchor members 12, including two, three or five or more anchor members. In one embodiment, the anchor members 12a-12d are coupled or interconnected to one another via a linking element 30. In the illustrated embodiment, the linking element 30 comprises a suture extending through the axial passages 22 in each of the anchor members 12a-12d to link the anchor members 12a-12d together in series. The linking element 30 provides structural integrity to the anchoring system 10 by controlling the position and/or orientation of the anchor members 12a-12d relative to one another, the details of which will be discussed below. Additionally, the linking element 30 has a length l such that the anchor members 12a-12d may be axially separated or spaced from one another in a non-abutting manner, the purpose of which will also become apparent below.

In the illustrated embodiment of the invention, the ends 30a, 30b of the linking element 30 are attached to one another so to define a continuous suture loop having a first end loop 32 extending from the outer anchor member 12a and a second end loop 34 extending from the outer anchor member 12d. In the illustrated embodiment of the invention, the ends 30a, 30b are tied or knotted together to form the suture loop 30. However, it should be understood that the ends 30a, 30b of the suture loop 30 may be attached to one another using other techniques such as, for example, via the use of a crimp or another type of coupling device, by fusing or splicing the ends 30a, 30b together, or by any other suitable method of attachment. It should also be understood that the linking element 30 need necessarily be configured as a loop, but may alternatively define a non-looped, single strand configuration. It should further be understood that the anchor members 12a-12d need not necessarily be coupled together or interconnected via a single suture element, but may alternatively be individually coupled together via a number of discrete suture elements. Additionally, it should be understood that the anchor members 12a-12d need not necessarily be coupled together by suture material, but may alternatively be coupled together using other elements and techniques such as, for example, via a number of pins, hinges, fittings, eyelets or any other suitable coupling device.

In the illustrated embodiment of the invention, the anchoring system 10 also includes an actuating element 40 that cooperates with the linking element 30 to selectively manipulate the position and/or orientation of one or more of the anchor members 12a-12d. In the illustrated embodiment, the actuating element 40 comprises a suture that engages the end portions of the linking element 30 to selectively manipulate the position and/or orientation of one or more of the anchor members 12a-12d. In a specific embodiment, the actuating element 40 extends through the end loops 32, 34 of the linking element 30 such that pulling the ends 40a, 40b of the actuating element 40 draws the outer anchor members 12a, 12d toward one another and transitions one or more of the anchor members 12a-12d to a different position and/or orientation, the details of which will be discussed below. Although the actuating element 40 is illustrated and described as being engaged with the end loops 32, 34 of the linking element 30, it should be understood that the actuating element 40 may alternatively be coupled to the outer anchor members 12a, 12d via other suitable techniques for drawing the outer anchor members 12a, 12d toward one another and for selectively transitioning one or more of the anchor members 12a-12d to a different position and/or orientation. For example, a full or partial loop element may be attached directly to the outer anchor members 12a, 12d through which the actuating element 40 extends.

In the illustrated embodiment of the invention, the anchoring system 10 further includes a second actuating element 50 that cooperates with the linking element 30 to selectively manipulate the position and/or orientation of one or more of the anchor members 12a-12d. In the illustrated embodiment, the actuating element 50 comprises a suture that engages the linking element 30 at a location between the inner anchor member 12b, 12c to selectively manipulate the position and/or orientation of one or more of the anchor members 12a-12d. In one embodiment, the actuating element 50 is looped about the linking element 30 such that pulling the ends 50a, 50b of the actuating element 50 draws the inner anchor members 12b, 12c to a location between the outer anchor members 12a, 12d. In a specific embodiment, the actuating element 50 is threaded between the strands of the suture loop linking element 30. Although the actuating element 50 is illustrated and described as being looped about the linking element 30, it should be understood that the actuating element 50 may be coupled to the linking element 30 via other techniques suitable for drawing the inner anchor members 12b, 12c between the outer anchor members 12a, 12d. For example, instead of looping the actuating element 50 about the linking element 30, an end portion of the actuating element 50 may by tied or otherwise secured to the linking element 30.

Having illustrated and described the various elements and features associated with the suture anchoring system 10, reference will now be made to a technique for engaging the anchoring system 10 to human body tissue. As indicated above, the anchoring system 10 is used to anchor a suture in either hard or soft biological tissue. In the illustrated embodiment of the invention, the anchoring system 10 is used to anchor a suture to bone in a human body. In a specific embodiment, the anchoring system 10 is used to anchor a suture to a portion of one or more vertebrae in the spinal column. However, it should be understood that other applications of the anchoring system 10 are also contemplated, including anchoring to other bones or anatomic structures within the human body. Additionally, it should be understood that use of the anchoring system 10 in other animals is also contemplated as falling within the scope of the present invention.

Figure 2:
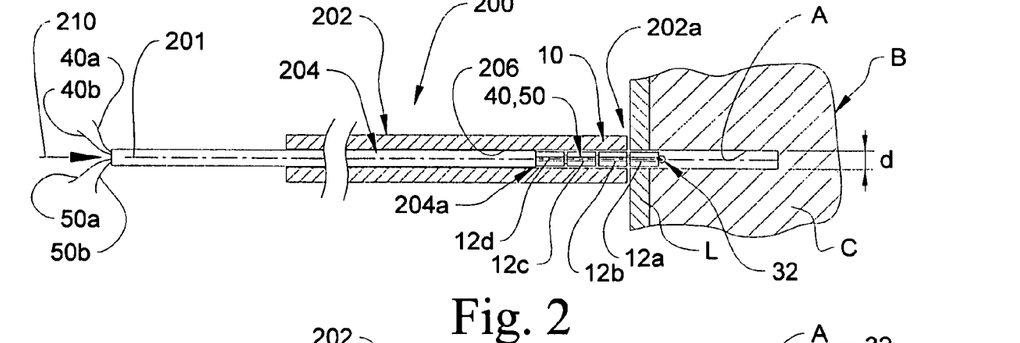
FIG. 2 is an illustration of the suture anchoring system shown in FIG. 1, as loaded within a cannula tube in an insertion configuration for delivery through an aperture in body tissue.

Referring to FIG. 2, the anchoring system 10 is illustrated as being used in association with a bone B having a relatively hard and compact outer cortical layer L surrounding a softer and more porous inner cancellous region C. In one embodiment of the invention, an axial tunnel or aperture A having a maximum transverse dimension d may be preformed through the cortical layer L and into the cancellous region C for receiving the anchoring system 10. However, in an alternative embodiment, the anchoring system 10 may be inserted directly into the body tissue without creating a preformed tunnel or aperture, particularly in applications involving relatively soft body tissue.

In the illustrated embodiment of the invention, the anchoring system 10 is delivered to the surgical site via a delivery instrument 200 extending along a longitudinal axis 201 and generally comprising an outer sleeve or cannula member 202 and an inner rod member 204. The cannula member 202 defines an axial passageway 206 extending therethrough and having an inner cross section sized somewhat larger than the outer transverse cross section of the individual anchor members 12. The inner rod member 204 is sized and configured to be slidably positioned within the axial passageway 206 of the cannula member 202. In one embodiment, the inner rod member 204 has a circular outer cross section that corresponds to the inner cross section of the cannula member 202. However, other configurations of the cannula member 202 and/or the inner rod member 204 are also contemplated as falling within the scope of the present invention.

The outer transverse cross section of the individual anchor members 12 is sized somewhat smaller than the inner cross section of the axial passageway 206 in the cannula member 202 to allow the anchor members 12 to freely slide along the axial passageway 206. Additionally, sufficient clearance exists between the anchor members 12 and the cannula member 202 to provide spacing for the passage of the suture elements 40 and 50. In the illustrated embodiment, the axial passageway 206 has a circular inner cross section corresponding to the circular outer cross section of the anchor members 12. However, it should be understood that the axial passageway 206 may be configured to have a different inner cross section such as, for example, a rectangular, triangular or polygonal inner cross section, or any other inner cross section suitable for receiving and conveying the anchor members 12 therethrough. Additionally, in an alternative embodiment of the invention, the outer transverse cross section of the anchor members 12 and the inner cross section of the axial passageway 206 can be configured different from one another to provide a predetermined spacing therebetween for passage of the suture elements 40 and 50. For example, in one alternative embodiment, the axial passageway 206 can be configured to have a circular inner cross section whereas the anchor members 12 can be configured to have a generally triangular or rectangular outer cross section.

The anchor members 12a-12d are initially positioned within the distal end portion of the cannula member 202 in an axially-aligned or linear configuration, with the axes of the anchor members 12a-12d generally aligned along the longitudinal axis 201. The end portions 40a, 40b and 50a, 50b of the suture elements 40 and 50 extend from the proximal end (not shown) of the cannula member 202 for subsequent manipulation by the surgeon. The distal end portion 202a of the cannula member 202 is positioned proximally adjacent the bone B, with the axial passageway 206 generally aligned with the aperture A. However, in an alternative embodiment of the invention, the distal end portion 202a of the cannula member 202 may be positioned within the aperture A formed through the outer cortical layer L and possibly extending partially into the cancellous region C of the bone B.

Figure 3:
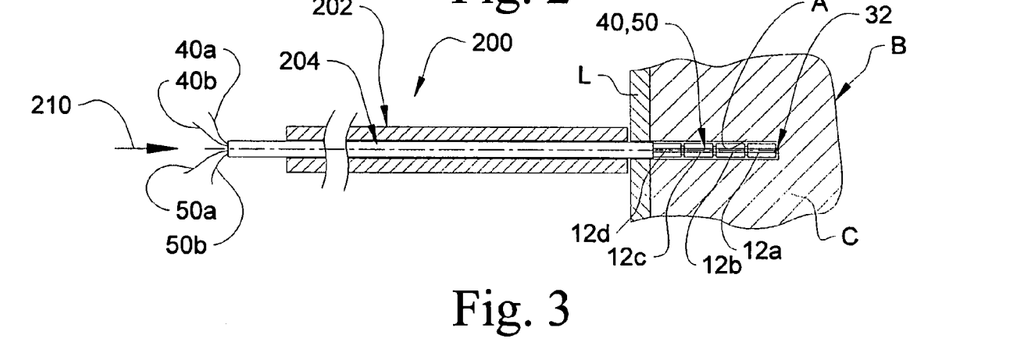
FIG. 3 is an illustration of the suture anchoring system shown in FIG. 2, with the anchor members delivered through the aperture in the body tissue.

Referring to FIG. 3, once the cannula member 202 is properly positioned relative to the aperture A, the inner rod member 204 is axially displaced in the direction of arrow 210 with the distal end 204a engaging the anchor member 12d, which in turn displaces the anchor members 12a-12d through the axial passageway 206. The inner rod member 204 is axially advanced in the direction of arrow 210 until the anchor members 12a-12d are deployed from the cannula member 202 and into the aperture A in the cancellous region C of the bone B. As illustrated in FIG. 3, the depth of the aperture A in the cancellous region C is preferably sized to entirely receive the anchor members 12a-12d therein in the axially-aligned configuration. The rod member 204 may then be removed from the cannula member 202 or can remain in position until the anchoring process is completed to prevent the anchor members 12a-12d from passing back through the cortical layer L of the bone B.

Figure 4:
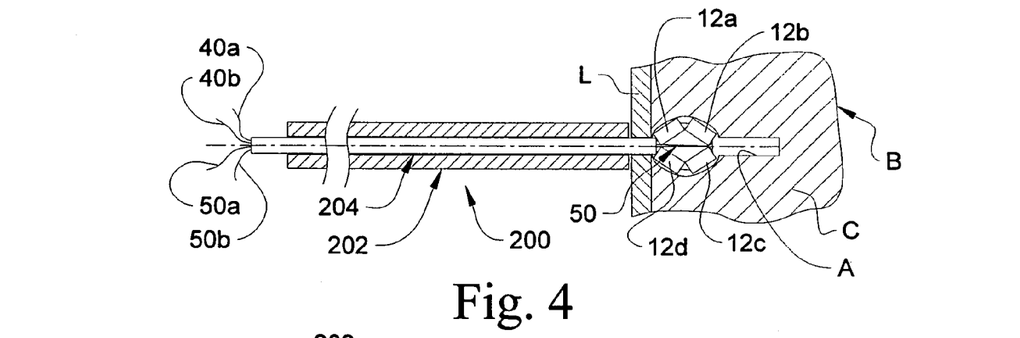
FIG. 4 is an illustration of the suture anchoring system shown in FIG. 3, with the anchor members transitioned to a first anchoring configuration.

Referring to FIG. 4, once the anchor members 12a-12d are deployed from the cannula member 202 and properly positioned within the aperture A in the cancellous region C of the bone B, the anchor members 12a-12d are selectively transitioned to a non-linear or expanded configuration. As should be appreciated, transitioning of the anchor members 12a-12d to the non-linear configuration results in outward compression against the relatively soft cancellous bone tissue, thereby resulting in enlargement of the aperture A in the bone B. However, as should also be appreciated, for applications involving anchoring to denser or harder bone tissue, an enlarged portion of the aperture A may have to be preformed in the bone B to allow for transitioning of the anchor members 12a-12d to the expanded, non-linear configuration.

Transitioning of the anchor members 12a-12d is effectuated by pulling the ends 40a, 40b of the actuating suture element 40 in a proximal direction so as to reconfigure the anchor members 12a-12d from the axially-aligned configuration illustrated in FIG. 3 to the expanded configuration illustrated in FIG. 4. More specifically, since the suture element 40 extends through the end loops 32, 34 of the linking element 30, pulling the suture element 40 in a proximal direction draws the outer anchor members 12a, 12d toward one another. As a result, the anchor members 12a-12d are repositioned/reoriented so as to define a generally U-shaped configuration, with the anchor members 12a, 12b being arranged generally laterally opposite the anchor members 12c, 12d.

Figure 5:
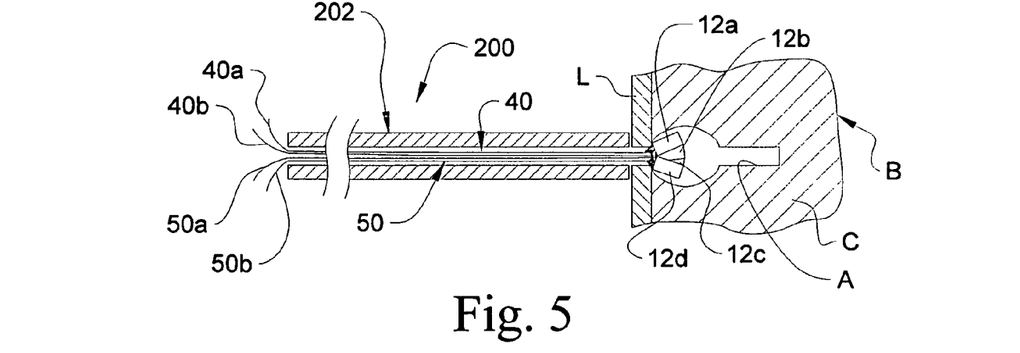
FIG. 5 is an illustration of the suture anchoring system shown in FIG. 4, with the anchor members transitioned to a second anchoring configuration.

Once transitioned to the non-linear configuration illustrated in FIG. 4, the anchor members 12a-12d are further transitioned to the expanded configuration illustrated in FIG. 5 by pulling the ends 50a, 50b of the actuating suture element 50 in a proximal direction. As should be appreciated, pulling the suture element 50 in a proximal direction reconfigures the anchor members 12a-12d from the U-shaped expanded configuration illustrated in FIG. 4 to the denser configuration illustrated in FIG. 5. Pulling the actuating element 50 in a proximal direction draws the inner anchor members 12b, 12c between the outer anchor members 12a, 12d. More specifically, the inner anchor members 12b, 12c are repositioned and reoriented relative to the outer anchor members 12a, 12d so as to position the inner anchor members 12b-12c in a laterally adjacent or side-by-side relationship relative to the outer anchor members 12a, 12d. As should be appreciated, the expanded configuration of the anchor members 12a-12d illustrated in FIG. 5 is somewhat larger than the inner cross section of the aperture A extending through the outer cortical layer L of the bone B. Accordingly, the expanded configuration of the anchor members 12a-12d will not pass through the aperture A in the cortical bone layer L, thereby securely anchoring the anchor members 12a-12d and the suture elements 40 and 50 to the bone B. The suture elements 40 and 50 may then be attached to other elements/structures so as to secure such elements/structures to the bone B, examples of which will be set forth below.

Figure 6:
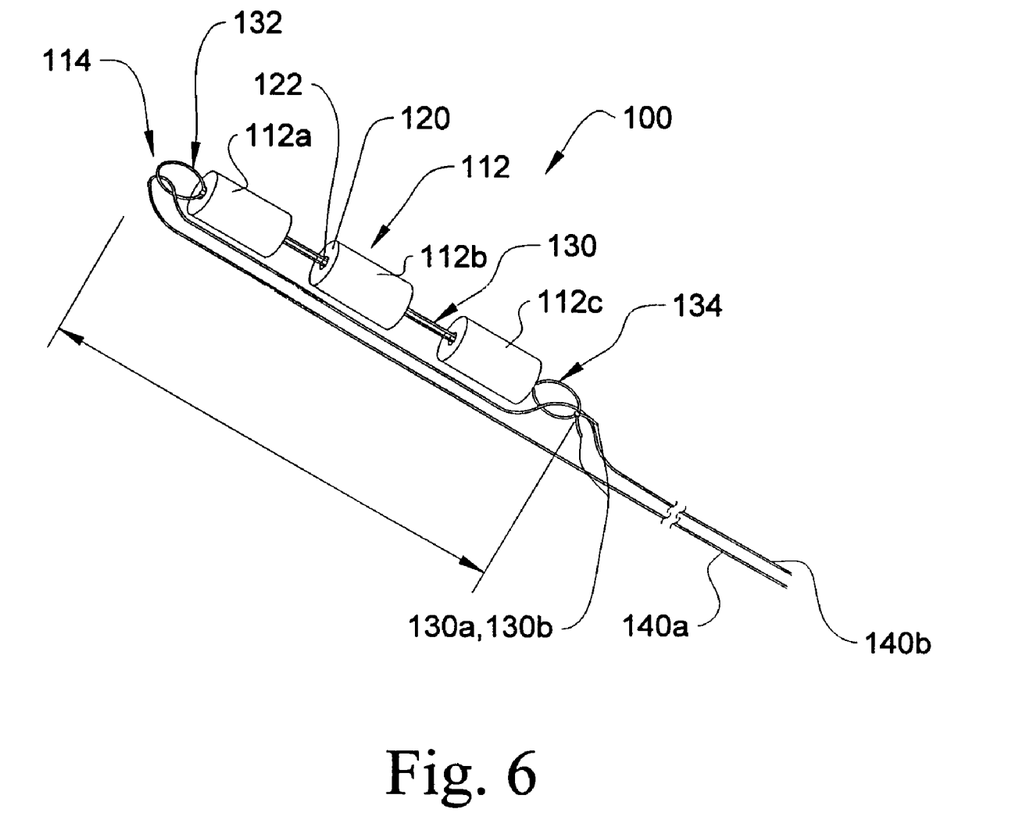
FIG. 6 is a perspective view of a suture anchoring system according to another form of the present invention.

Referring to FIG. 6, shown therein is a suture anchoring system 100 according to another form of the present invention. The anchoring system 100 is generally comprised of a plurality of anchor members 112 and a number of suture elements 114. As will be discussed in greater detail below, in one embodiment of the invention, the anchoring system 100 is configured for anchoring to either hard or soft biological tissue, with the suture elements 114 serving to attach another element or structure (either biological or non-biological) to the biological tissue.

In the illustrated embodiment of the invention, the anchor members 112 are configured identical to the anchor members 12 illustrated and described above with regard to the anchoring system 10, with each anchor member 112 having a generally tubular configuration including a cylindrical wall 120 and defining an axial passage or channel 122 extending therethrough. However, it should be understood that other shapes and configurations of the anchor members 112 are also contemplated as falling within the scope of the present invention including, for example, a rectangular, triangular, polygonal or spherical configuration, or any other suitable shape or configuration. The anchor members 112 are preferably formed of a bio-compatible material. In one embodiment, the anchor members 112 are formed of metallic material such as stainless steel or a stainless steel alloy, titanium or a titanium alloy, a shape-memory alloy, or any other suitable metallic material. However, the use of other materials is also contemplated, including polymeric or ceramic materials, resorbable materials, bioabsorbable materials, or bone or bone substitute materials.

In the illustrated embodiment of the invention, the suture anchoring system 100 includes three anchor members 112a, 112b and 112c that are coupled together or interconnected to form an anchor assembly. However, it should be understood that the anchoring system 100 may include any number of anchor members 112, including two or four or more anchor members. In one embodiment, the anchor members 112a-112c are coupled or interconnected to one another via a linking element 130. In the illustrated embodiment, the linking element 130 comprises a suture extending through the axial passages 122 in each of the anchor members 112a-112c to link the anchor members 112a-112c together in series. The linking element 130 provides structural integrity to the anchoring system 100 by controlling the position and/or orientation of the anchor members 112a-112c relative to one another, the details of which will be discussed below. Additionally, the linking element 130 has a length l' such that the anchor members 112a-112c may be axially separated or spaced from one another in a non-abutting manner, the purpose of which will become apparent below.

In the illustrated embodiment of the invention, the ends 130a, 130b of the linking element 130 are attached to one another so to define a continuous suture loop having a first end loop 132 extending from the outer anchor member 112a and a second end loop 134 extending from the outer anchor member 112c. In the illustrated embodiment of the invention, the ends 130a, 130b are tied or knotted together to form the suture loop 130. However, it should be understood that the ends 130a, 130b of the suture loop 130 may be attached to one another using other techniques such as, for example, via the use of a crimp or another type of coupling device, by fusing or splicing the ends 130a, 130b together, or by any other suitable method of attachment. It should also be understood that the linking element 130 need necessarily be configured as a loop, but may alternatively define a non-looped, single strand configuration. It should be further understood that the anchor members 112a-112c need not necessarily be coupled together or interconnected via a single suture element, but may alternatively be individually coupled together via a number of discrete suture elements. Additionally, it should be understood that the anchor members 112a-112c need not necessarily be coupled together by suture material, but may alternatively be coupled together using other elements and techniques such as, for example, via a number of pins, hinges, fittings, eyelets or any other suitable coupling device.

In the illustrated embodiment of the invention, the anchoring system 100 also includes an actuating element 140 that cooperates with the linking element 130 to selectively manipulate the position and/or orientation of one or more of the anchor members 112a-112c. In the illustrated embodiment, the actuating element 140 comprises a suture that engages the end portions of the linking element 130 to selectively manipulate the position and/or orientation of one or more of the anchor members 112a-112c. In a specific embodiment, the actuating element 140 extends through the end loops 132, 134 of the linking element 130 such that pulling the ends 140a, 140b of the actuating element 140 draws the outer anchor members 112a, 112c toward one another and transitions one or more of the anchor members 112a-112c to a different position and/or orientation, the details of which will be discussed below. Although the actuating element 140 is illustrated and described as being connected to the end loops of the linking element 130, it should be understood that the actuating element 140 may be coupled to the outer anchor members 112a, 112c via other suitable techniques for drawing the outer anchor members 112a, 112c toward one another and for selectively transitioning one or more of the anchor members 112a-112c to a different position and/or orientation. For example, a full or partial loop element may be attached directly to the outer anchor members 112a, 112c through which the actuating element 140 extends.

Figure 7:
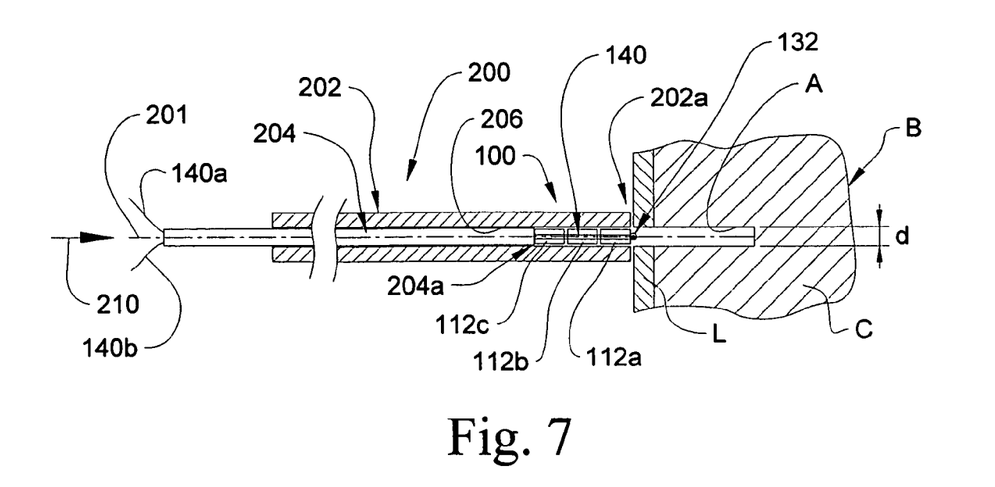
FIG. 7 is an illustration of the suture anchoring system shown in FIG. 6, as loaded within a cannula tube in an insertion configuration for delivery through an aperture in body tissue.

Having illustrated and described the various elements and features associated with the suture anchoring system 100, reference will now be made to a technique for engaging the anchoring system 100 to biological tissue such as, for example, to the bone B. However, as discussed above with regard to the anchoring system 10, it should be understood that other applications of the anchoring system 100 are also contemplated, including anchoring to other bones or anatomic structures. Referring to FIG. 7, in one embodiment of the invention, the anchoring system 100 is delivered to the surgical site via the delivery instrument 200 illustrated and described above. The anchor members 112a-112c are initially positioned within the distal end portion of the cannula member 202 in an axially-aligned or linear configuration, with the axes of the anchor members 112a-112c generally aligned along the longitudinal axis 201. The end portions 140a, 140b of the suture element 40 extend from the proximal end (not shown) of the cannula member 202 for subsequent manipulation by the surgeon. The distal end portion 202a of the cannula member 202 is positioned proximally adjacent the bone B, with the axial passageway 206 generally aligned with the aperture A extending into the cortical layer L.

Figure 8:
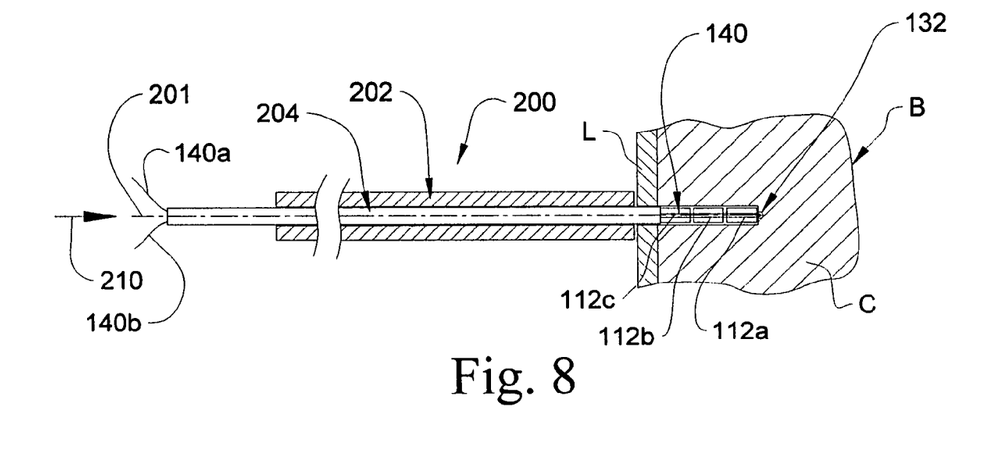
FIG. 8 is an illustration of the suture anchoring system shown in FIG. 7, with the anchor members delivered through the aperture in the body tissue.

Referring to FIG. 8, once the cannula member 202 is properly positioned relative to the aperture A, the inner rod member 204 is axially displaced in the direction of arrow 210 with the distal end 204a engaging the anchor member 112c, which in turn displaces the anchor members 112a-112c through the axial passageway 206. The inner rod member 204 is axially advanced in the direction of arrow 210 until the anchor members 112a-112c are deployed from the distal end 202a of cannula member 202 and into the cancellous region C of the bone B. As illustrated in FIG. 8, the depth of the aperture A in the cancellous region C is preferably sized so as to receive the axially-aligned anchor members 112a-112c therein. The rod member 204 may then be removed from the cannula member 202 or can remain in position until the anchoring process is completed to prevent the anchor members 112a-112c from passing back through the cortical layer L of the bone B.

Figure 9:
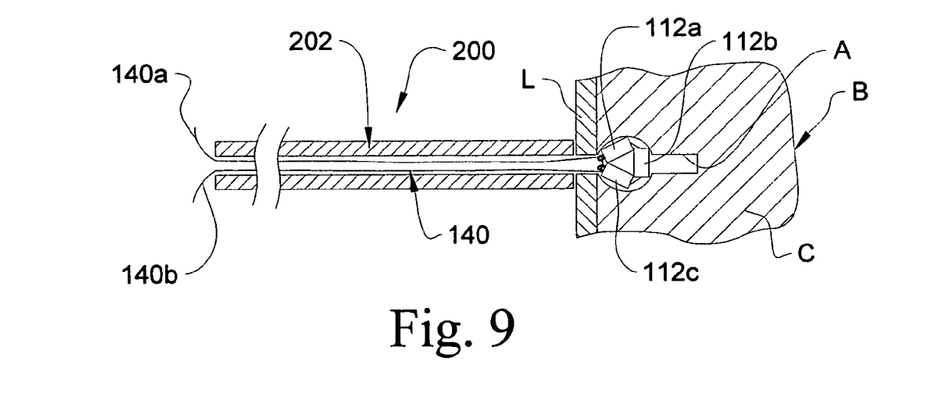
FIG. 9 is an illustration of the suture anchoring system shown in FIG. 8, with the anchor members transitioned to an anchoring configuration.

Referring to FIG. 9, once the anchor members 112a-112c are deployed from the distal end of the cannula member 202 and properly positioned within the aperture A in the cancellous region C of the bone B, the anchor members 112a-112c are transitioned to a non-linear or expanded configuration. Such transitioning is effectuated by pulling the ends 140a, 140b of the actuating suture element 140 in a proximal direction to reconfigure the anchor members 112a-112c from the axially-aligned configuration illustrated in FIG. 8 to the expanded configuration illustrated in FIG. 9. More specifically, since the suture element 140 extends through the end loops 132, 134 of the linking element 130, pulling the suture element 140 in a proximal direction draws the outer anchor members 112a, 112c toward one another. As a result, the anchor members 112a-112c are repositioned/reoriented so as to define a generally triangular-shaped configuration, with the outer anchor members 112a, 112c being angled toward one another and with the inner anchor member 112b extending laterally between the outer anchor members 112a, 1112c.

As should be appreciated, the expanded configuration of the anchor members 112a-112c illustrated in FIG. 9 is larger than the inner cross section of the aperture A extending through the outer cortical bone layer L. Accordingly, the expanded configuration of the anchor members 112a-112c will not pass through the aperture A in the cortical bone layer L, thereby securely anchoring the anchor members 112a-112c and the suture element 140 to the bone B. The suture element 140 may be attached to other elements/structures so as to secure such elements/structures to the bone B.

As should now be appreciated, the anchoring systems 10, 100 illustrated and described above may be anchored to either hard or soft biological tissue, with the suture elements 40, 50 and 140 being used to attach another element or structure to the biological tissue. In one embodiment of the invention, the anchoring systems 10, 100 may be used to provide a surgical anchor useful in the repair and/or replacement of ligaments, tendons or other types of tissues. In another embodiment of the invention, the anchoring systems 10, 100 may be used to provide a surgical anchor for holding a bone block in place in a tunnel formed in bone such that a piece of soft tissue attached to the bone block can be connected to the bone under tension. In yet another embodiment of the invention, the anchoring systems 10, 100 may be used to provide a surgical anchor that avoids or reduces the risks associated with severing, twisting or otherwise damaging material associated with soft tissue repair or replacement. In still another embodiment of the invention, the anchoring systems 10, 100 may be used to provide a surgical anchor that may be inserted into a tunnel formed in bone that avoids or reduces the likelihood of seriously damaging the surrounding bone material. In a further embodiment of the invention, the anchoring systems 10, 100 may be used to provide a surgical anchor that is adapted to secure material used in association with tissue repair or replacement in close proximity to bone in such a manner as to promote the formation or growth of a permanent attachment therebetween. In another embodiment of the invention, the anchoring systems 10, 100 may be used in association with a method for repairing and/or replacing ligaments, tendons or other types of tissues by coupling an end portion of such tissue (or its replacement) to a tunnel extending into or through a bone or a bone-like structure.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A suture anchoring system, comprising:
   a suture;
   at least three anchor members interconnected to form an anchor assembly with said suture extending therefrom, wherein said at least three anchor members include first and second outer anchor members and at least one intermediate anchor member, and said anchor assembly having an insertion configuration sized for delivery through an aperture in bodily tissue and being transitionable to an expanded configuration sized to prevent passage of said anchor assembly back through the aperture;
   a first actuating element extending through a first loop structure associated with said first outer anchor member and through a second loop structure associated with said second outer anchor member; and a second actuating element secured to said anchor assembly adjacent said at least one intermediate anchor member; and wherein said first and second outer anchor members are drawn toward one another by pulling said first actuating element in a direction away from said anchor assembly to at least partially transition said anchor assembly toward said expanded configuration; and wherein said at least one intermediate anchor member is positioned laterally between said first and second outer anchor members by pulling said second actuating element in a direction away from said anchor assembly to further transition said anchor assembly toward said expanded configuration.

2. A suture anchoring system, comprising:

a suture;

at least three anchor members interconnected to form an anchor assembly with said suture extending therefrom, wherein said at least three anchor members include first and second outer anchor members and at least one intermediate anchor member, and said anchor assembly having an insertion configuration sized for delivery through an aperture in bodily tissue and being transitionable to an expanded configuration sized to prevent passage of said anchor assembly back through the aperture; and an actuating element extending through a first loop structure associated with said first outer anchor member and through a second loop structure associated with said second outer anchor member; and wherein said first and second outer anchor members are drawn toward one another by pulling said actuating element in a direction away from said anchor assembly to at least partially transition said anchor assembly toward said expanded configuration.

3. The system of claim 2, wherein each of said at least three anchor members has a tubular configuration defining an axial passage extending therethrough, said at least three anchor members being serially interconnected by a linking element extending through said axial passage in each of said at least three anchor members to form said anchor assembly, looped end portions of said linking element defining said first and second loop structures associated with said first and second outer anchor members.

4. The system of claim 3, wherein each of said linking element and said actuating element comprises a suture.

5. A suture anchoring system, comprising:

a suture;

at least three anchor members interconnected to form an anchor assembly with said suture extending therefrom, wherein said at least three anchor members include first and second outer anchor members and at least one intermediate anchor member, and said anchor assembly having an insertion configuration sized for delivery through an aperture in bodily tissue and being transitionable to an expanded configuration sized to prevent passage of said anchor assembly back through the aperture, wherein each of said at least three anchor members has a tubular configuration defining an axial passage extending therethrough, said at least three anchor members being serially interconnected by a linking element extending through said axial passage in each of said at least tree anchor members to form said anchor assembly; and an actuating element extending through a first looped end portion of said linking element adjacent said first outer anchor member and through a second looped end portion of said linking element adjacent said second outer anchor member;

wherein said first and second outer anchor members are drawn toward one another by pulling said actuating element in a direction away from said anchor assembly to at least partially transition said anchor assembly toward said expanded configuration.

6. A suture anchoring system, comprising:

a suture; and at least three anchor members interconnected to form an anchor assembly with said suture extending therefrom, said anchor assembly including first and second outer anchor members and at least one intermediate anchor member, said anchor assembly having an insertion configuration and an expanded configuration to prevent passage of said anchor assembly back through the aperture; and an actuating element extending through a first loop structure associated with said first outer anchor member and through a second loop structure associated with said second outer anchor member;

wherein said first and second outer anchor members are drawn toward one another by pulling said actuating element in a direction away from said anchor assembly to at least partially transition said anchor assembly toward said expanded configuration.

7. The system of claim 6, wherein each of said at least three anchor members has a tubular configuration defining an axial passage extending therethrough, Said at least three anchor members being serially interconnected by a linking element extending through said axial passage in each of said at least three anchor members to form said anchor assembly, looped end portions of said linking element defining said first and second loop structures associated with said first and second outer anchor members.

8. The system of claim 6, wherein said insertion configuration is one in which said anchor members aligned in a substantially linear arrangement for delivery through an aperture in bodily tissue.

9. The system of claim 6, wherein said expanded configuration is one in which first and second outer anchor members are drawn toward one another to define a non-linear arrangement.

10. A suture anchoring system, comprising:

a suture;

a plurality of anchor members interconnected to form an anchor assembly with said suture extending therefrom, said anchor assembly having an insertion configuration wherein said anchor members are aligned in a substantially linear arrangement for delivery trough an aperture in bodily tissue and an expanded configuration wherein first and second ones of said anchor members are drawn toward one another to define a non-linear arrangement to prevent passage of said anchor assembly back through the aperture; and an actuating element extending through a first loop structure associated with said first anchor member and through a second loop structure associated with said second anchor member, wherein said first and second anchor members are drawn toward one another by pulling said actuating element in a direction away from said anchor assembly to at least partially transition said anchor assembly toward said expanded configuration.

11. The system of claim 10, wherein said plurality of anchor members includes at least one intermediate anchor member positioned between said first and second anchor members, said non-linear arrangement of said anchor assembly comprises a triangular-shaped configuration with said at least one intermediate anchor member extending transversely between said first and second anchor members.

12. The system of claim 10, wherein said plurality of anchor members includes at least one intermediate anchor member positioned between said first and second anchor members, said non-linear arrangement of said anchor assembly comprises a side-by-side configuration with said at least one intermediate anchor member positioned laterally between said first and second anchor members.

13. The system of claim 10, wherein each of said anchor members has a tubular configuration defining an axial passage extending therethrough, said anchor members being serially interconnected by a linking element extending through said axial passage m each of said anchor members to form said anchor assembly, looped end portions of said linking element defining said first and second loop structures associated with said first and second anchor members.

14. The system of claim 13, wherein each of said linking element and said actuating element comprises a suture.

15. A suture anchoring system, comprising:
 a suture; and
 at least two anchor members interconnected to form an anchor assembly with said suture extending therefrom, said anchor assembly having an insertion configuration sized for delivery through an aperture in bodily tissue and being transitionable to an expanded configuration sized to prevent passage of said anchor assembly back through aperture, said suture forming at least one loop; and
 an actuating member extending through said at least one loop; and
 a second actuating member that engages said suture at a point between said anchor members.

16. The system of claim 15, wherein said second actuating member is looped about said suture.

17. A suture anchoring system, comprising:
 a suture; and
 at least two anchor members interconnected to form an anchor assembly with said suture extending therefrom, said anchor assembly having an insertion configuraton sized for delivery through an aperture in bodily tissue and being transitionable to an expanded configuration sized to prevent passage of said anchor assembly back through the aperture, said suture farming at least one loop; and
 an actuating member extending through said at least one loop; and
 wherein said ax least one loop of said suture comprises first and second loops, and said actuating member extends through both loops.

* * * * *

UNITED STATES PATENT AND TRADEMARK OFFICE
CERTIFICATE OF CORRECTION

PATENT NO.       : 7,658,750 B2                                    Page 1 of 1
APPLICATION NO.  : 10/803440
DATED            : February 9, 2010
INVENTOR(S)      : Lehmann K. Li It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1705 days.

Signed and Sealed this

Thirtieth Day of November, 2010

David J. Kappos
*Director of the United States Patent and Trademark Office*